US007052695B2

(12) United States Patent
Kalish

(10) Patent No.: US 7,052,695 B2
(45) Date of Patent: May 30, 2006

(54) ANGIOPOIETINS AND METHODS OF TREATING HYPERTENSION

(75) Inventor: Susan Croll Kalish, Tarrytown, NY (US)

(73) Assignee: Regeneron Pharmaceuticals, Inc., Tarrytown, NY (US)

(*) Notice: Subject to any disclaimer, the term of this patent is extended or adjusted under 35 U.S.C. 154(b) by 390 days.

(21) Appl. No.: 10/274,222

(22) Filed: Oct. 18, 2002

(65) Prior Publication Data

US 2003/0082177 A1     May 1, 2003

Related U.S. Application Data

(60) Provisional application No. 60/348,415, filed on Oct. 25, 2001.

(51) Int. Cl.
*A61K 38/18* (2006.01)
*A61K 39/395* (2006.01)
*C07K 14/515* (2006.01)

(52) U.S. Cl. ............... 424/178.1; 514/12; 530/388.22; 530/391.1; 530/530

(58) Field of Classification Search ............ 514/2, 514/12; 424/178.1; 530/350, 387.3; 435/69.7
See application file for complete search history.

(56) References Cited

U.S. PATENT DOCUMENTS 6,482,406 B1 * 11/2002 Stewart 6,592,864 B1 * 7/2003 Stewart

FOREIGN PATENT DOCUMENTS

| WO | WO 96/11269 | 4/1996 |
| WO | WO96/31598 | 10/1996 |
| WO | WO 97/48804 | 12/1997 |
| WO | WO 98/05779 | 2/1998 |
| WO | WO 00/37642 | 6/2000 |

OTHER PUBLICATIONS

Koblizek et al., Angiopoietin-1 induces sprouting angiogenesis in vitro, Curr. Biol., 9:529-532, 1998.*
Jain et al., Leaky vessels? Call Ang1! Nat. Med., 6(2):131-132, Feb. 2000.*
Angiopoietin-1 protects the adult vasculature against plasma leakage, Nat. Med., 6(4):460-463, Apr. 2000.*
Zhang et al., Angiopoietin-1 reduces crebral blood vessel leakage and ischemic lesion volume after focal cerebral embolic ischemia in mice, Neurosci., 113(3):683-687, 2002.*
Ganong, W.F.(1995), Review of Medical Physiology, 17th Ed. (Appleton & Lange:Norwalk CT), p. 630.*

(Continued)

*Primary Examiner*—Lorraine Spector
*Assistant Examiner*—Claire M. Kaufman
(74) *Attorney, Agent, or Firm*—Valeta Gregg, Esq.

(57) ABSTRACT

The invention generally relates to angiogenic factors and more particularly to the angiopoietin family of growth factors and to methods of using these growth factors to induce vasodilation and hypotension and reducing hypertension.

5 Claims, 9 Drawing Sheets

OTHER PUBLICATIONS

Kido et al., Gene transfer of a TIE2 receptor antagonist prevents pulmonary hypertension in rodents, J. Thor. Cardiovascular Surg. 129:268-76, Feb 2005.*

Rudge et al., Angiopoietin-1 and pulmonary hypertension: Cause or Cure? Circ. Res. 92:947-949, 2003.*

Zhao et al., Protective role of angiopoietin-1 in experimental pulmonary hypertension, Circ. Res. 92:984-91, 2003.*

Videm, V. A new animal model for pulmonary hypertension based on the overexpression of a single gene, angiopoietin-1: Invited commentary, Ann. Thorac. Surg. 77(2):456-457, 2004.*

Humbert et al., Cellular and molecular pathobiology of pulmonary arterial hypertension, J. Am. Coll. Cardiol. 43:13S-24S, 2004.*

Davis, S., et al., 1996, "Isolation of angiopoietin-1, a ligand for the TIE2 receptor, by secretion trap expression cloning", Cell 87:1161-1169.

* cited by examiner

ANGIOPOIETINS AND METHODS OF TREATING HYPERTENSION

This application claims priority of U.S. Provisional Application No. 60/348,415, filed Oct. 25, 2001. Throughout this application various patents and other publications are referenced. The disclosures of each and all of these patents and other publications in their entireties are hereby incorporated by reference into this application.

FIELD OF THE INVENTION

The invention generally relates to angiogenic factors and more particularly to the angiopoietin family of growth factors and to methods of using these growth factors to induce vasodilation.

BACKGROUND OF THE INVENTION

Hypertension

Hypertension is a condition that occurs when the blood pressure inside the large arteries is too high. Hypertension is very common, affecting about 50 million people in the United States alone. It is more common as people grow older and is both more common and more serious in African Americans. Most cases of hypertension are of unknown etiology. It is known that the tendency to develop hypertension can be inherited. Environment also plays a very important role in hypertension. For example, hypertension may be avoided by keeping body weight under control, keeping physically fit, eating a healthy diet, limiting alcohol intake, and avoiding medications that might increase blood pressure. Other less common causes of hypertension include disorders of the kidneys or endocrine glands. Hypertension has been called "the silent killer" because it has no specific symptoms and yet can lead to death. People with untreated hypertension are much more likely to die from or be disabled by cardiovascular complications such as strokes, heart attacks, heart failure, heart rhythm irregularities, and kidney failure, than people who have normal blood pressure.

Current treatments for hypertension include lifestyle changes (diet, exercise, nonsmoking, etc.) as well as drug therapy. The major classes of medications currently used to treat hypertension include adrenergic neuron antagonists (which are peripherally acting), alpha adrenergic agonists (which are centrally acting), alpha adrenergic blockers, alpha & beta blockers, angiotensin II receptor blockers, angiotensin converting enzyme (ACE) inhibitors, beta adrenergic blockers, calcium channel blockers, Thiazide and related diuretics, and vasodilators (which act by direct relaxation of vascular smooth muscles).

A particularly serious hypertensive disorder is primary pulmonary hypertension, also known as idiopathic pulmonary hypertension. This is a condition in which the blood pressure in the pulmonary arteries is abnormally high in the absence of other diseases of the heart or lungs. The cause of primary pulmonary hypertension is unknown. Pulmonary hypertension develops in response to increased resistance to blood flow. Narrowing of the pulmonary arterioles occurs and the right side of the heart becomes enlarged due to the increased work of pumping blood against the resistance. Eventually, progressive heart failure develops. Currently, there is no known cure for primary pulmonary hypertension. Treatment is primarily directed towards controlling the symptoms, although some success has occurred with the use of vasodilators. Other medications used to treat the symptoms of primary pulmonary hypertension include diuretics and calcium channel blockers. Typically, as the disease progresses, oxygen if often required. In certain cases, a heart-lung transplant may be indicated for certain suitable candidates, although the availability of donor organs continues to be extremely limited. Unfortunately, primary pulmonary hypertension is a progressive disease, usually leading to congestive heart failure and respiratory failure.

Secondary pulmonary hypertension is a serious disorder that arises as a complication of other conditions such as, for example, scleroderma. Treatments are similar as those for primary pulmonary hypertension and, unfortunately, the prognosis is the same as well.

Chronic circulatory disorders

Ischemia is a condition in which the blood flow within an artery is limited to the point where the oxygen needs of the organ it serves cannot be met, thus resulting in hypoxia. Different types of ischemia have different names, depending on which organ in the body is deprived of oxygen. For example, reduced blood flow to the brain is called cerebral ischemia, which can lead to either a warning stroke called a transient ischemic attack (TIA) or possibly a full stroke. Cardiac ischemia is a situation in which the blood flow within a coronary artery is limited to the point where the oxygen needs of the heart muscle cannot be met. Cardiac ischemia can lead to myocardial infarction (heart attack). Other types of ischemia include hepatic ischemia and renal ischemia. Additionally, ischemia within the lower extremities (e.g., the legs) can cause muscle cramping when walking and in more severe cases can cause pain in the feet even at rest. In the most extreme cases gangrene can form. This occurs when local tissues are deprived of oxygen such that they die. Unfortunately, gangrene often leads to amputation of the involved limb. This type of ischemia is common in diabetics.

Minor episodes of cardiac ischemia tend to cause little long-term damage to the heart, but these episodes can sometimes cause serious problems. For example, they can cause arrhythmias, which can lead to either fainting or even cardiac arrest. However, severe or lengthy episodes of cardiac ischemia can trigger a heart attack. The collective effects of minor episodes of cardiac ischemia can potentially lead to a weakening of the heart muscle, a condition known as cardiomyopathy. Extreme cases of cardiomyopathy can require a heart transplant to save the individuals life.

Because cardiac ischemia occurs when the heart is not getting enough oxygen, one treatment may be to reduce the heart's need for oxygen. This treatment involves taking medications that slow heart rate, reduce blood pressure, and relax the blood vessels (vasodilation). The three main classes of drugs that accomplish this are called beta-blockers, calcium channel blockers, and nitrates. In addition, aspirin and other anti-platelets are very useful in decreasing blood clot formation, thus reducing the chance of blocked arteries triggering a heart attack. Exercise and/or stress management techniques may be helpful as well. More invasive techniques such as a balloon angioplasty or bypass surgery may be recommended if the less invasive treatments are unsuccessful.

Other, less serious, ischemic conditions exist as well. Buerger's disease, or thromboangiitis obliterans, is characterized by an inflammatory response in the arteries, veins, and nerves, which leads to a thickening of the blood vessel walls caused by infiltration of white blood cells. The cause of Buerger's disease is unknown, but because it occurs mostly in young men who smoke, it is thought to be a reaction to something in cigarettes or the result of a genetic or autoimmune disorder. The first symptoms are usually a bluish cast to a toe or finger and a feeling of coldness in the affected limb. As the blood vessels become blocked, intermittent claudication (a condition caused by diminished blood supply to the leg muscles as a result of the narrowing of arteries of the legs; marked by pain and lameness during mobility, but absence of pain when sedentary) and other symptoms similar to those of chronic obstructive arterial disease often appear. Ischemic ulcers and gangrene are common complications of progressive Buerger's disease. The most effective and important treatment is to smoking cessation; if this is done early in the disease before serious blood vessel or nerve damage has occurred, the symptoms usually improve markedly. If pain and circulatory problems persist, surgery to sever the sympathetic nerves that cause the small blood vessels to constrict may be performed.

Raynaud's phenomenon is characterized by spasms of the arteries in the fingers and toes, causing a lack of blood flow to the affected parts. There are two classifications of this disorder: primary, in which there is no evidence of other underlying disease; and secondary, in which the condition is complicated by other disorders, such as lupus erythematosus, rheumatoid arthritis, or scleroderma. Sometimes Raynaud's may accompany Buerger's disease. Excessive constriction of the vessels serving the fingers and toes causes spasms, which are usually triggered by cold, smoking cigarettes, or, less frequently, emotional factors. Raynaud's phenomenon may be an indication of an underlying disease. The symptoms include coldness, blueness, a tingling sensation, numbness, and sometimes pain in the digits. Corresponding fingers on both hands are usually affected. Primary Raynaud's may be uncomfortable or annoying, but rarely leads to serious problems such as chronic ulcers or gangrene. Many people with Raynaud's phenomenon get some relief by using a calcium-channel blocker such as nifedipine. Another medication called phenoxybenzamine may also help by limiting the constricting effects of adrenaline on the blood vessels. In some cases, the circulation may be impaired enough to cause sores or ulcers to form; in a small minority, these may progress to gangrene and amputation.

Acute Ischemias

Stroke syndrome is caused by a disorder of the blood vessels serving the brain, resulting in cerebral ischemia. Cerebral ischemia is also called stroke, cerebral vascular accident, and cerebrovascular accident. There are four neurological events associated with stroke: transient ischemic attack (TIA), reversible ischemic neurologic deficit (RIND), stroke in evolution (SIE), and completed stroke (CS). TIAs are temporary attacks that come on suddenly and last only a few minutes to not more than 24 hours; although they often are not recognized as such, they are a warning that a completed stroke can occur. RIND is an event similar to TIA except that the symptoms last for several days to a week; there is complete or nearly complete recovery. Like TIA, RIND is an indication that the person is at high risk for a completed stroke. A person with a stroke in evolution (SIE) experiences gradual weakness on one side of the body. The diagnosis of SIE is confirmed when the progressive changes are witnessed by the physician. The person with a completed stroke (CS) exhibits symptoms associated with severe cerebral ischemia resulting from an interrupted blood supply to the brain. Persons most at risk for any of the four types of stroke include those with hypertension, atherosclerosis, and heart disease and other cardiovascular disorders. Obese persons, heavy smokers, and those with diabetes mellitus are also at increased risk.

Medical and surgical preventive measures have significantly reduced the incidence of stroke in the United States. Medical preventive measures are aimed at eliminating or controlling atherosclerosis and other conditions that predispose a person to stroke. Effective control of hypertension and treatment of rheumatic and atherosclerotic heart disease have significantly reduced the incidence of stroke. Efforts to control diabetes mellitus, reduce cholesterol levels by diet and exercise, manage obesity, and encourage cessation of smoking are all examples of measures that have been successful in preventing stroke in significant numbers of people at risk. The choice of medical prevention and treatment is governed by the conditions that predispose the patient to having a stroke and, in the event one has already occurred, the potential of the individual patient to benefit from the treatment.

Other disorders associated with vascular dysfunction and insufficiency

Penile erectile dysfunction is a disorder characterized by an inability to achieve or maintain an erection and most commonly occurs when the penis is deprived of oxygen-rich blood. A number of conditions can deprive the penis of oxygen-rich blood. The primary cause of oxygen deprivation is ischemia—the blockage of blood vessels. The same conditions, such as unhealthy cholesterol levels, that cause blockage in the blood vessels leading to heart problems may also contribute to erectile dysfunction. As the plaque builds up, the arterial walls slowly constrict, reducing blood flow; this process, known as atherosclerosis, is the major contributor to the development of coronary heart disease. It may also play a role in the development of erectile dysfunction.

Nitric Oxide

The importance of endothelial nitric oxide (NO) generation in sustaining a tonic systemic vasodilatation is well established. Inhibiting NO production produces hypertension in animals and in humans and not surprisingly there has been considerable interest in establishing whether deficiencies of endothelial NO pathway activity are implicated in the etiology of hypertension.

Angiopoietins

An angiogenic factor, which was originally called TIE-2 ligand-1 (TL1) but is also referred to as angiopoietin-1 (Ang1), has been previously identified. Ang1 signals through the endothelial cell-specific receptor called the TIE-2 receptor and is essential for normal vascular development. By homology screening, an Ang1 relative has also been identified and is called TIE-2 ligand-2 (TL2) or angiopoietin-2 (Ang2). Ang2 is a naturally occurring context-specific antagonist for Ang1 and the TIE-2 receptor. For a description of the cloning and sequencing of TL1 (Ang1) and TL2 (Ang2) as well as for methods of making and uses thereof, reference is hereby made to PCT International Publication No. WO 96/11269 published Apr. 18, 1996 and PCT International Publication No. WO 96/31598 published Oct. 10, 1996 both in the name of Regeneron Pharmaceuticals, Inc.; and S. Davis, et al., Cell 87: 1161–1169 (1996) each of which is hereby incorporated by reference. In addition to the naturally occurring angiopoietins, several mutant molecules have been engineered that exhibit improved properties over the angiopoietins. For example, Ang1* is a mutant form of Ang1 that comprises the N-terminal domain of Ang2 fused to the coiled-coil domain and the fibrinogen domain of Ang1 and that has a Cys to Ser mutation at amino acid 245. Ang1* has been shown to be a potent agonist for the Tie-2 receptor (See U.S. Pat. No. 6,265,564, issued Jul. 24, 2001, to Davis, et al. which is hereby incorporated by reference).

In addition to the above-described angiopoietins, several related angiogenic factors have been identified. These have been designated Tie ligand-3 (TL3, Ang3) and Tie ligand-4 (TL4, Ang4). For descriptions of the structure and functional properties of these four related factors, reference is hereby made to the following publications, each of which is hereby incorporated by reference: U.S. Pat. No. 5,851,797, issued Dec. 22, 1998, in the name of Davis, et al.; PCT International Application No. PCT/US95/12935, filed Oct. 6, 1995, published on Apr. 18, 1996, with Publication No. WO 96/11269; PCT International Application No. PCT/US96/04806, filed Apr. 5, 1996, published on Oct. 10, 1996, with Publication No. WO96/31598; PCT International Application No. PCT/US97/10728, filed Jun. 19, 1997, published on Dec. 24, 1997 with Publication No. WO 97/48804. All PCT applications filed in the name of Regeneron Pharmaceuticals, Inc.

The angiopoietins can be structurally divided into three domains: an N-terminal region lacking in homology to any known structures; an alpha helical rich coil-coil segment similar to motifs found in many proteins that seem to promote multimerization; and a "fibrinogen-like domain" thus dubbed because it is distantly related to a domain first found in fibrinogen but now noted to be in many other proteins (Davis, S. et al., (1996) Cell 87:1161–1169). The fibrinogen-like domain represents the most conserved region of the angiopoietins, and recent studies indicate that it comprises the receptor-binding portion of an angiopoietin. In addition, all the information that determines whether an angiopoietin is an agonist or an antagonist appears to reside within the fibrinogen-like domain. For example, when chimeric molecules are made in which the fibrinogen-like domains of angiopoietin-1 and angiopoietin-2 are swapped, agonistic or antagonistic abilities track with the fibrinogen-like domains. The N-terminal and coil-coil regions appear to serve mainly to multimerize the fibrinogen-like domains, which apparently must be clustered to be active. In fact, the N-terminal and coil-coil regions can be substituted for by alternative motifs that allow clustering. Thus, the activities of Ang1 and Ang2 can be precisely mimicked by surrogates in which the fibrinogen-like domains (FD) of these factors are fused to the constant region of an antibody, resulting in FD-Fc fusions, which can then be clustered using secondary antibodies directed against the Fc. For a general description of the production and use of FD-Fc fusions, see International Publication Number WO 97/48804 published Dec. 24, 1997. Using these techniques, one of skill in the art would be able to similarly make FD-Fc fusions using the fibrinogen-like domain of an angiopoietin family member. One practical advantage of such surrogates is that native angiopoietins can be difficult to produce recombinantly, while the surrogates can be more easily produced.

As described supra, experiments with mutants of Ang1 and Ang2 have demonstrated that the fibrinogen domains (FD) are the receptor-binding domains, and that dimerized versions (dimerization occurs due to the interaction between the Fc components of adjacent molecules), for example Ang1-FD-Fc, can bind to the TIE2 receptor with much higher affinity than monomeric Ang1-FD. However, Ang1-FD-Fc is not able to induce phosphorylation (activate) the TIE2 receptor on endothelial cells unless it is further clustered with goat anti-human Fc antibodies (Jackson Immunoresearch). For this reason, mutant versions of Ang1-FD and Ang2-FD were designed that were intrinsically more highly clustered.

Two general types of nucleic acid molecules were constructed. The first type consisted of two tandem copies of Ang1-FD fused to an Fc tag, thus leading to a secreted polypeptide molecule that is dimeric with respect to the Fc tag but tetrameric with respect to Ang1-FD. Similarly, two tandem copies of Ang2-FD fused to an Fc tag constituted the Ang2 version of this type of construct. These molecules were designated Ang1-FD-FD-Fc and Ang2-FD-FD-Fc, respectively.

In the second type of nucleic acid molecule constructed, two copies of Ang1-FD were connected by an Fc tag bridging between them, thus creating the structure Ang1-FD-Fc-FD that is still dimeric with respect to the Fc, as well as tetrameric with respect to Ang1-FD. An Ang2 version was also constructed and these two molecules were designated Ang1-FD-Fc-FD and Ang2-FD-Fc-FD, respectively.

For either type of construct, similar properties were observed: unlike dimeric Ang1-FD-Fc, which fails to activate TIE2 on endothelial cells, both Ang1-FD-FD-Fc and Ang1-FD-Fc-FD could readily activate TIE2 on endothelial cells, with a potency comparable to that of the native ligand. Also, like native Ang-2, Ang2-FD-Fc-FD could behave as a context-specific antagonist of Ang1 activity with a potency that is comparable to that of native Ang2, and with much greater potency than the marginally antagonistic activity of the Ang2-FD-Fc dimer.

In accordance with the subject invention, Applicants describe herein methods of treating vascular diseases, in particular, hypertension and ischemia, by the administration of TIE2 receptor activating molecules. Such molecules include, but are not limited to, Ang1, Ang1*, Ang1-FD-Fc-FC and other suitable fragments and derivatives capable of activating TIE2.

SUMMARY OF THE INVENTION

The invention generally relates to angiogenic factors and more particularly to the angiopoletin family of growth factors and to methods of using these growth factors to induce vasodilation.

One preferred embodiment of the method of the invention is a method of inducing vasodilation in a mammal comprising administering to the mammal an TIE2 receptor activator capable of inducing vasodilation.

Also preferred is a method of increasing blood flow to ischemic tissue in a mammal comprising administering to the mammal an TIE2 receptor activator capable of increasing blood flow to ischemic tissue.

Another preferred embodiment is one wherein the ischemic tissue is cardiac tissue, hepatic tissue, renal tissue, or skeletal muscle tissue.

Yet another preferred embodiment of the invention is a method of inducing hypotension in a mammal comprising administering to the mammal a TIE2 receptor activator capable of inducing hypotension.

Also preferred is a method of attenuating acute hypertension in a mammal comprising administering to the mammal a TIE2 receptor activator capable of attenuating acute hypertension.

Still another preferred embodiment of the invention is a method of treating vascular insufficiency in a mammal comprising administering to the mammal a TIE2 receptor activator capable of treating vascular insufficiency.

Another preferred embodiment is a method wherein the vascular insufficiency is penile erectile dysfunction, Raynaud's Syndrome, or diabetic vascular insufficiency.

Also preferred is a method of attenuating chronic hypertension in a mammal comprising administering to the mammal a TIE2 receptor activator capable of attenuating chronic hypertension.

One preferred embodiment is wherein the chronic hypertension is pulmonary hypertension including primary pulmonary hypertension and secondary pulmonary hypertension.

Another preferred embodiment is one in which the TIE2 receptor activator is Ang-1, Ang-1*, or Ang1-FD-Fc-FD; a small molecule; an activating antibody or a fragment thereof, including a scFv fragment of an antibody; and wherein the antibody is a monoclonal antibody.

A preferred embodiment of the invention is one wherein the mammal is a human.

The description and examples presented infra are provided to illustrate the subject invention. One of skill in the art will recognize that these examples are provided by way of illustration only and are not included for the purpose of limiting the invention.

DETAILED DESCRIPTION OF THE INVENTION

Figure 1:
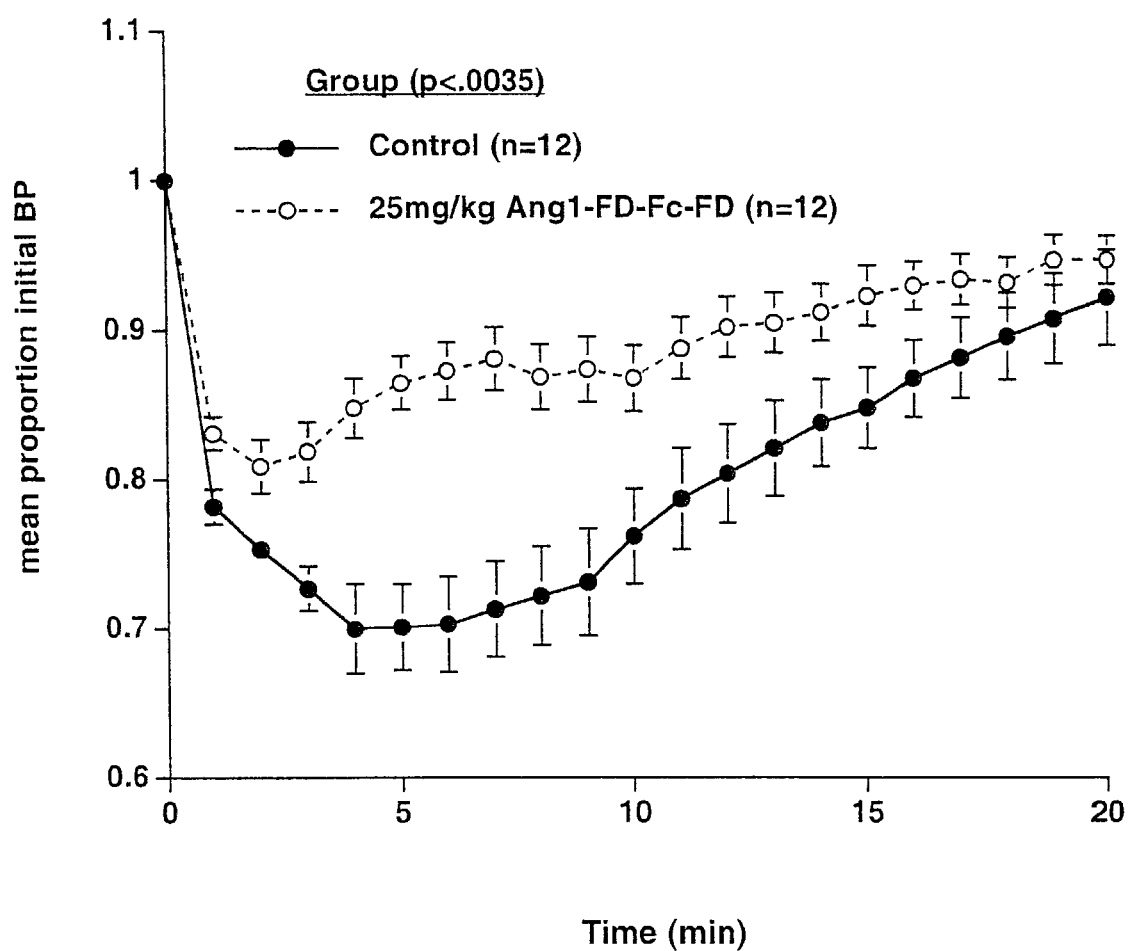
FIG. 1. VEGF-induced hypotension as a function of pre-treatment with Ang1-FD-Fc-FD. Ang1-FD-Fc-FD pre-treatment (open circles) significantly attenuates VEGF-induced hypotension relative to vehicle controls (closed circles). Data are presented as proportion of the systolic blood pressure recorded at the time of VEGF injection at time 0.

As described in greater detail below, Applicant has invented a method of inducing vasodilation in a mammal comprising administering to the mammal a TIE2 receptor activator. In one preferred embodiment of the invention, the mammal is a human and the TIE2 receptor activator is Ang1, Ang1*, or Ang1-FD-Fc-FD.

The invention further provides for a method wherein the TIE2 receptor activator is Ang1, or a fragment or derivative thereof capable of activating the TIE2 receptor.

The invention also provides for a method wherein the TIE-2 receptor activator is an activating antibody, or a fragment or derivative thereof capable of activating the TIE-2 receptor, including a single chain Fv (scFv).

The invention further provides for a method wherein the TIE-2 receptor activator is a small molecule, or a fragment or derivative thereof capable of activating the TIE2 receptor.

By way of example, but not limitation, the method of the invention may be useful in treating clinical conditions that are characterized by hypertension, including pulmonary hypertension, and ischemic conditions including chronic ischemias such as diabetic ischemia, Bueger's Syndrome and Raynaud's Syndrome, and acute ischemias such as those associated with myocardial infarction and stroke. Other clinical applications include treatment of penile erectile dysfunction associated with decreased blood flow.

The present invention comprises TIE2 ligands such as, for example, Ang1, Ang1*, and Ang1-FD-Fc-FD as well as their amino acid sequence and also functionally equivalent molecules in which amino acid residues are substituted for residues within the sequence resulting in a silent change. For example, one or more amino acid residues within the sequence can be substituted by another amino acid(s) of a similar polarity that acts as a functional equivalent, resulting in a silent alteration. Substitutes for an amino acid within the sequence may be selected from other members of the class to which the amino acid belongs. For example, the class of nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Antibodies, including monoclonal antibodies, that activate the TIE2 receptor are also contemplated by the invention. For preparation of monoclonal antibodies, any technique which provides for the production of antibody molecules by continuous cell lines in culture may be used. For example, the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in "Monoclonal Antibodies and Cancer Therapy," Alan R. Liss, Inc. pp. 77–96) and the like are within the scope of the present invention.

The monoclonal antibodies may be human monoclonal antibodies or chimeric human-mouse (or other species) monoclonal antibodies. Human monoclonal antibodies may be made by any of numerous techniques known in the art (e.g., Teng et al., 1983, Proc. Natl. Acad. Sci. U.S.A. 80:7308–7312; Kozbor et al., 1983, Immunology Today 4:72–79; Olsson et al., 1982, Meth. Enzymol. 92:3–16). Chimeric antibody molecules may be prepared containing a mouse antigen-binding domain with human constant regions (Morrison et al., 1984, Proc. Natl. Acad. Sci. U.S.A. 81:6851, Takeda et al., 1985, Nature 314:452).

Various procedures known in the art may be used for the production of polyclonal antibodies. For the production of TIE2 activating antibodies, various host animals, including but not limited to rabbits, mice and rats can be immunized by injection with TIE2 receptor extracellular domain, or a fragment or derivative thereof. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

A molecular clone of an antibody to a selected epitope can be prepared by known techniques. Recombinant DNA methodology (see e.g., Maniatis et al., 1982, Molecular Cloning, A Laboratory Manual, Cold Spring Harbor Laboratory, Cold Spring Harbor, N.Y.) may be used to construct nucleic acid sequences which encode a monoclonal antibody molecule, or antigen-binding region thereof.

The present invention provides for antibody molecules as well as fragments of such antibody molecules. Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Antibody molecules may be purified by known techniques, e.g., immunoabsorption or immunoaffinity chromatography, chromatographic methods such as HPLC (high performance liquid chromatography), or a combination thereof.

The method of the invention also contemplates the use of antibody fragments directed against Tie-2 called single chain Fvs. A single chain Fv (scFv) is a truncated Fab having only the V region of an antibody heavy chain linked by a stretch of synthetic peptide to a V region of an antibody light chain. See, for example, U.S. Pat. Nos. 5,565,332; 5,733,743; 5,837,242; 5,858,657; and 5,871,907 assigned to Cambridge Antibody Technology Limited incorporated by reference herein.

Ang1, Ang1*, or Ang1-FD-Fc-FD pharmaceutical compositions can be prepared. Ang1, Ang1*, or Ang1-FD-Fc-FD-containing pharmaceutical compositions typically include a therapeutically effective amount of Ang1, Ang1*, or Ang1-FD-Fc-FD combined with one or more pharmaceutically and physiologically acceptable formulation components selected for suitability with the mode of administration. Suitable formulation components include, but are not limited to, preservatives, diluting agents, emulsifying agents, suspending agents, solvents, fillers, bulking agents, buffers, delivery vehicles, excipients and/or pharmaceutical adjuvants. By way of non-limiting example, a suitable delivery vehicle may be water for injection or physiological saline solution. Buffered saline or saline mixed with serum albumin are other examples of suitable vehicles.

The vehicle solvent may be either aqueous or non-aqueous. In addition, the vehicle may contain other pharmaceutically acceptable components for maintaining the pH, osmolarity, viscosity, stability, etc. The vehicle may contain additional pharmaceutically acceptable components for affecting the rate of release of Ang1, Ang1*, or Ang1-FD-Fc-FD, or for promoting the absorption or penetration of Ang1, Ang1*, or Ang1-FD-Fc-FD.

Once the therapeutic composition has been formulated, it may be stored as a solution, suspension, gel, emulsion, solid, or dehydrated, or lyophilized powder. Such formulations may be stored either in a ready to use form or in a form requiring reconstitution or other manipulation prior to administration.

The optimal pharmaceutical formulations will be determined by skilled artisans. Such optimal formulations will depend upon, for example, route of administration and dosage. (See, for example, Remington's Pharmaceutical Sciences, 18th Ed. (1990, Mack Publishing Co., Easton, Pa. 18042) pages 1435–1712, the disclosure of which is hereby incorporated by reference).

The pharmaceutical composition also may be formulated for slow-release or sustained circulation formulations. It is also contemplated that certain formulations may be administered orally. Ang1, Ang1*, or Ang1-FD-Fc-FD, which is administered orally, may be formulated as an elixir, tablet, capsule, or gel. The capsule may be designed to release the active portion of the formulation in the gastrointestinal tract when bioavailability is maximized and degradation is minimized. Additional components may be included to facilitate absorption of Ang1, Ang1*, or Ang1-FD-Fc-FD. Such components include, but are not limited to, diluents, vegetable oils, lubricants, suspending agents, tablet disintegrating agents, and binders.

The Ang1, Ang1*, or Ang1-FD-Fc-FD may be administered parenterally via a subcutaneous, intramuscular, intravenous, intraarterial, intranasal, intrapulmonary, or intraperitoneal route. Alternatively, Ang1, Ang1*, or Ang1-FD-Fc-FD may be administered orally, or into specific areas of the gastrointestinal tract, or via rectal, transdermal or topical routes. The frequency of dosing will depend on the pharmacokinetic parameters of the Ang1, Ang1*, or Ang1-FD-Fc-FD as formulated, and the route of administration used.

The specific dose may be calculated according to considerations of body weight, body surface area, or organ size. Further refinement of the calculations necessary to determine the appropriate dosage for treatment involving each of the above mentioned formulations and routes of administration is routinely made by those of ordinary skill in the art. Appropriate dosages may be determined through the use of established assays for determining dosages utilized in conjunction with appropriate dose-response data.

The final dosage regimen involved in a method for treating the above-described conditions will be determined by the attending physician, considering various factors which modify the action of drugs, e.g., the age, condition, body weight, sex and diet of the patient, the severity of the disorder or disease, time of administration, and other clinical factors. As studies are conducted, further information will emerge regarding the appropriate dosage levels for the treatment of the various diseases and conditions.

Toxicity of the compounds described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds that exhibit high therapeutic indices are preferred. The data obtained from these cell culture assays and animal studies can be used in formulating a dosage range that is not toxic for use in humans. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch.1, p.1).

It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the clinical disorder of interest will vary with the severity of the condition to be treated and the route of administration. The severity of the condition may, for example, be evaluated, in part, by appropriate prognostic evaluation methods. Further, the dose and perhaps dose frequency, will also vary according to the age, body weight, and response of the individual patient.

In addition to conventional treatment modalities and routes of administration such as those described supra, numerous methods exist for genetically engineering mammalian cells. There is great interest in genetically engineering mammalian cells for several reasons including the need to produce large quantities of various polypeptides and the need to correct various genetic or other defects in the cells or in tissues and organs. The methods differ dramatically from one another with respect to such factors as efficiency, level of expression of foreign genes, and the efficiency of the entire genetic engineering process. Viral vectors are presently the most frequently used means for transforming cells and introducing DNA into the genome. In an indirect method, viral vectors, carrying new genetic information, are used to infect target cells removed from the body, and these cells are then reimplanted. Direct in vivo gene transfer into postnatal animals has been reported for formulations of DNA encapsulated in liposomes and DNA entrapped in proteoliposomes containing vital envelope receptor proteins (Nicolau et al., Proc. Natl. Acad Sci USA 80:1068–1072 (1983); Kaneda et al., Science 243:375–378 (1989); Mannino et al., Biotechniques 6:682–690 (1988). Positive results have also been described with calcium phosphate co-precipitated DNA (Benvenisty and Reshef Proc. Natl. Acad Sci USA 83:9551–9555 (1986)). One method of genetically engineering mammalian cells that has proven to be particularly useful is by means of retroviral vectors. Retrovirus vectors and their uses are described in many publications including Mann, et al., Cell 33:153–159 (1983) and Cone and Mulligan, Proc. Natl. Acad. Sci. USA 81:6349–6353 (1984). Retroviral vectors are produced by genetically manipulating retroviruses. Retroviruses are RNA viruses; that is, the viral genome is RNA. This genomic RNA is, however, reverse transcribed into a DNA copy that is integrated stably and efficiently into the chromosomal DNA of transduced cells. Retroviral vectors are particularly useful for modifying mammalian cells because of the high efficiency with which the retroviral vectors "infect" target cells and integrate into the target cell genome. Additionally, retroviral vectors are highly useful because the vectors may be based on retroviruses that are capable of infecting mammalian cells from a wide variety of species and tissues. The ability of retroviral vectors to insert into the genome of mammalian cells have made them particularly promising candidates for use in the genetic therapy of genetic diseases in humans and animals.

Another commonly used viral vector system in the Adeno-associated virus (AAV). The broad host range, low incidence of immune response, and longevity of gene expression observed with this vector have enabled the initiation of several clinical trials using this gene delivery system. Another potential benefit of using AAV vectors is their ability to integrate in a site-specific manner when introduced in the presence of Rep proteins. In addition, adenoviral vectors are used in many experimental settings to mimic acute administration of a protein of interest in vivo for the purpose of studying biological effects of the protein.

EXAMPLES

Example 1

Ang1-FD-Fc-FD-induced Hypotension

Materials and Methods

Subjects—Male Wistar-Kyoto rats, 250–300 g, were double-housed in a temperature and humidity-controlled animal housing room. Animals were maintained on a 12:12 light:dark cycle (lights on 06:00). Food and water were available ad libitum.

Systemic injections—Animals that received pre-treatment with Ang1-FD-Fc-FD were treated with 25 mg/kg Ang1-FD-Fc-FD sub-cutaneously 48 hours prior to surgery, 24 hours prior to surgery, and the morning of surgery. Surgeries to invasively monitor blood pressure were conducted approximately 4 hours after the last injection of Ang1-FD-Fc-FD.

Blood Pressure Measurement—Anesthesia was induced with 2.5% isoflurane in oxygen. Animals were then transferred to a nose cone delivering 1.5–2% isoflurane. Fur was shaved from the left inner thigh and from the right clavicular region. An incision was made in the inner aspect of the thigh, exposing the femoral vein and artery. The femoral artery was isolated and a silicone medical tubing was inserted into the artery. The tubing was filled with heparinized saline and was connected to a blood pressure transducer (IITC). After transduction, the signal was sent to a 4-channel chart recorder (Linseis) for continuous monitoring of pulse and systolic blood pressure. Exact blood pressure values were calculated based on a calibrated standard determined in advance of the surgery using a sphygmomanometer.

After blood pressure stabilized (same value for 1–2 minutes), animals were injected intravenously via the right jugular vein with either 10 μg vascular endothelial growth factor (VEGF), 10 μg acidic FGF (αFGF), 5 mg L-NAME, or 40 μg Ang1-FD-Fc-FD. Studies were conducted as follow:
1) Ang1-FD-Fc-FD s.c. pre-treatment followed by i.v. VEGF
2) Ang1-FD-Fc-FD s.c. pre-treatment followed by i.v. VEGF or αFGF
3) Ang1-FD-Fc-FD or VEGF i.v.
4) i.v. Ang1-FD-Fc-FD or VEGF followed 1–24 hours later by repeat injection
5) i.v. L-NAME followed 6 minutes later by i.v. Ang1-FD-Fc-FD or VEGF
6) i.v. Ang1-FD-Fc-FD or VEGF followed 6 minutes later by i.v. L-NAME For each experiment, animals were monitored for 10 minutes after the last treatment administered. Some animals were monitored for up to 3 hours to track the longevity of the Ang1-FD-Fc-FD-induced hypotension.

Data Analysis—The systolic blood pressure was determined for the point immediately prior to the first i.v. injection, and for every minute thereafter. Because animals can have varying initial systolic blood pressures, blood pressures were then normalized to the starting initial blood pressure, which was defined as that which occurred just prior to injection of Ang1-FD-Fc-FD, VEGF, or αFGF i.v. Normalized blood pressures were analyzed using a Mixed Factorial ANOVA (treatment×time). In addition, initial systolic blood pressures were analyzed either by a Student's independent groups t-test or an independent groups ANOVA, depending on the number of groups in each experiment. For all analyses, alpha was set at 0.05.

Results

VEGF-induced hypotension is attenuated by Ang1-FD-Fc-FD: The precise mechanism of VEGF-induced hypotension is unknown. It is known that VEGF can mediate both vasodilation and vascular leak through a nitric oxide-mediated mechanism. Because Ang1-FD-Fc-FD has been previously shown to interfere with VEGF-mediated vascular leak, Applicant hypothesized that Ang1-FD-Fc-FD would interfere with VEGF-induced hypotension if some or all of the hypotension was caused by vascular leak. 12 animals were injected with Ang1-FD-Fc-FD and 12 animals were injected with vehicle s.c. daily for 3 days before induction of VEGF-induced hypotension. Pre-treatment with Ang1-FD-Fc-FD significantly attenuated VEGF-induced hypotension ($F(1,22)=11.045$, $p<0.003$, FIG. 1). Initial systolic blood pressures were reduced in Ang1-FD-Fc-FD animals, but not significantly so ($t(22)=$, $p>0.13$).

Figure 2:
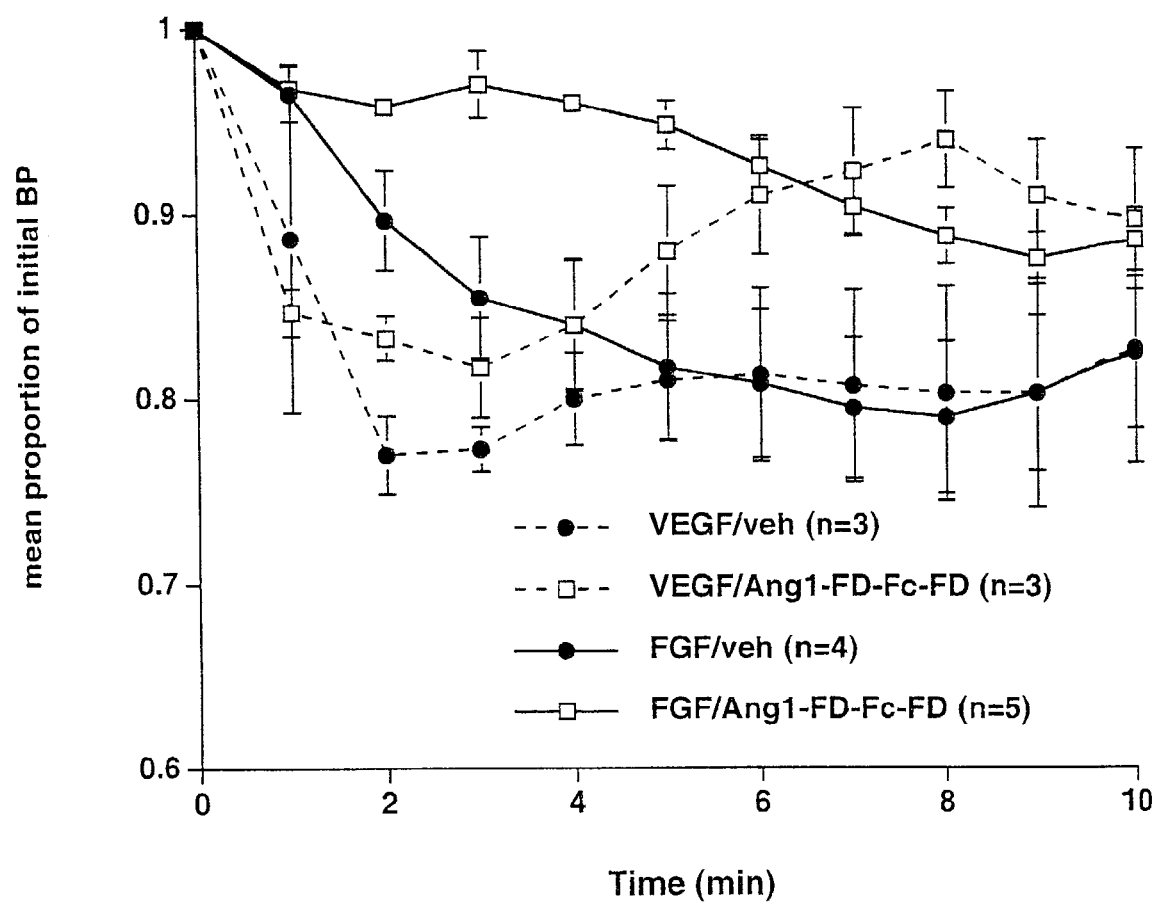
FIG. 2. Ang1-FD-Fc-FD pre-treatment dramatically attenuates FGF-induced hypotension, but only partially decreases VEGF-induced hypotension relative to vehicle pre-treatment.

Ang1-FD-Fc-FD blocks αFGF-induced hypotension: Because Ang1-FD-Fc-FD significantly attenuated VEGF-induced hypotension, Applicant theorized that much of VEGF's hypotensive effect is caused by vascular leak. However, it was difficult to be certain about this conclusion in the absence of a negative control. Like VEGF, both acidic and basic FGF cause acute hypotension when injected in an i.v. bolus. In addition, this hypotension is thought to result from nitric oxide-mediated vasodilation, one of the mechanisms proposed to contribute to VEGF-induced hypotension. Unlike VEGF, FGF has been shown not to induce vascular leak. Therefore, Applicant pre-treated animals with Ang1-FD-Fc-FD or vehicle s.c. daily for 3 days before inducing hypotension with VEGF or αFGF. Once again, Ang1-FD-Fc-FD reduced VEGF's hypotensive effects. Contrary to Applicant's expectations, Ang1-FD-Fc-FD dramatically interfered with FGF-induced hypotension. Ang1-FD-Fc-FD's effects were again statistically significant ($F(1,11)=5.094$, $p<0.05$, FIG. 2). Therefore, it seemed unlikely that Ang1-FD-Fc-FD's reduction of VEGF-induced hypotension was entirely the result of decreased vascular leak.

Figure 3:
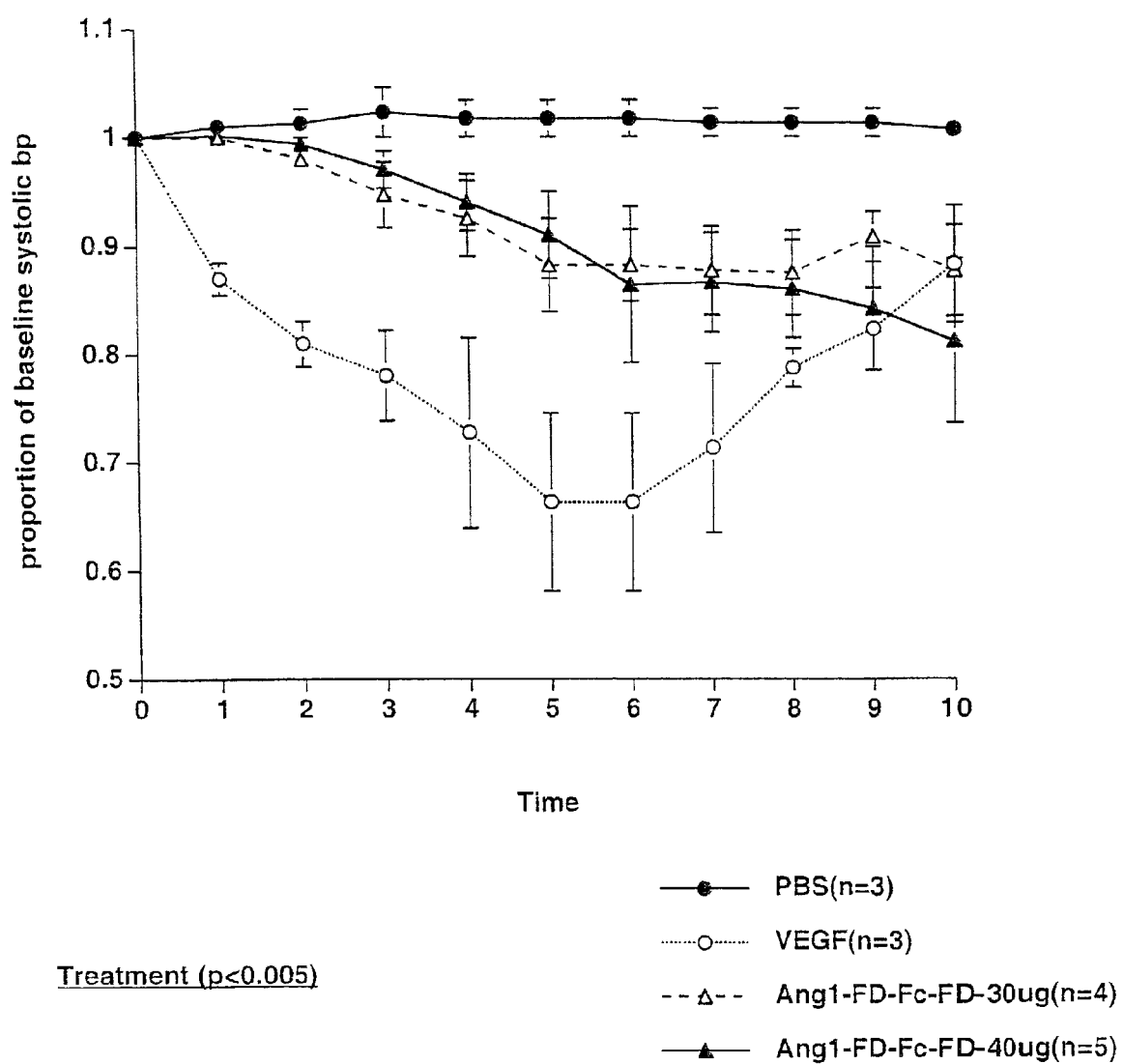
FIG. 3. Ang1-FD-Fc-FD induces significant hypotension, although milder than what VEGF induces, after an i.v. bolus injection. Ang1-FD-Fc-FD injected at 30–40 μg and VEGF injected at 10 μg.

Ang1-FD-Fc-FD induces hypotension: Acute administration of VEGF i.v. induces acute hypotension which recovers within 20–60 minutes. However, additional attempts to re-induce hypotension with VEGF fail for several hours after the initial reduction, suggesting that some of the actions of either VEGF or of hypotension remain in place for a period of time. These could include reduced receptor availability because of receptor turnover or the induction of compensatory mechanisms. Because Ang1-FD-Fc-FD interfered both with VEGF and FGF-induced hypotension, Applicants considered the possibility that Ang1-FD-Fc-FD itself was inducing hypotension, which then rendered the system refractory to attempts to induce hypotension with VEGF or FGF. When Ang1-FD-Fc-FD was acutely administered in a 40 μg i.v. bolus, significant hypotension developed ($F(3,11)=7.723$, $p<0.005$, FIG. 3). Further, unlike both VEGf and FGF, Ang1-FD-Fc-FD was acutely longer-lasting hypotension. Several animals were monitored for up to 3 hours after Ang1-FD-Fc-FD administration, and it was discovered that the approximately 15–20% decrease in blood pressure was maintained throughout this time.

Figure 4:
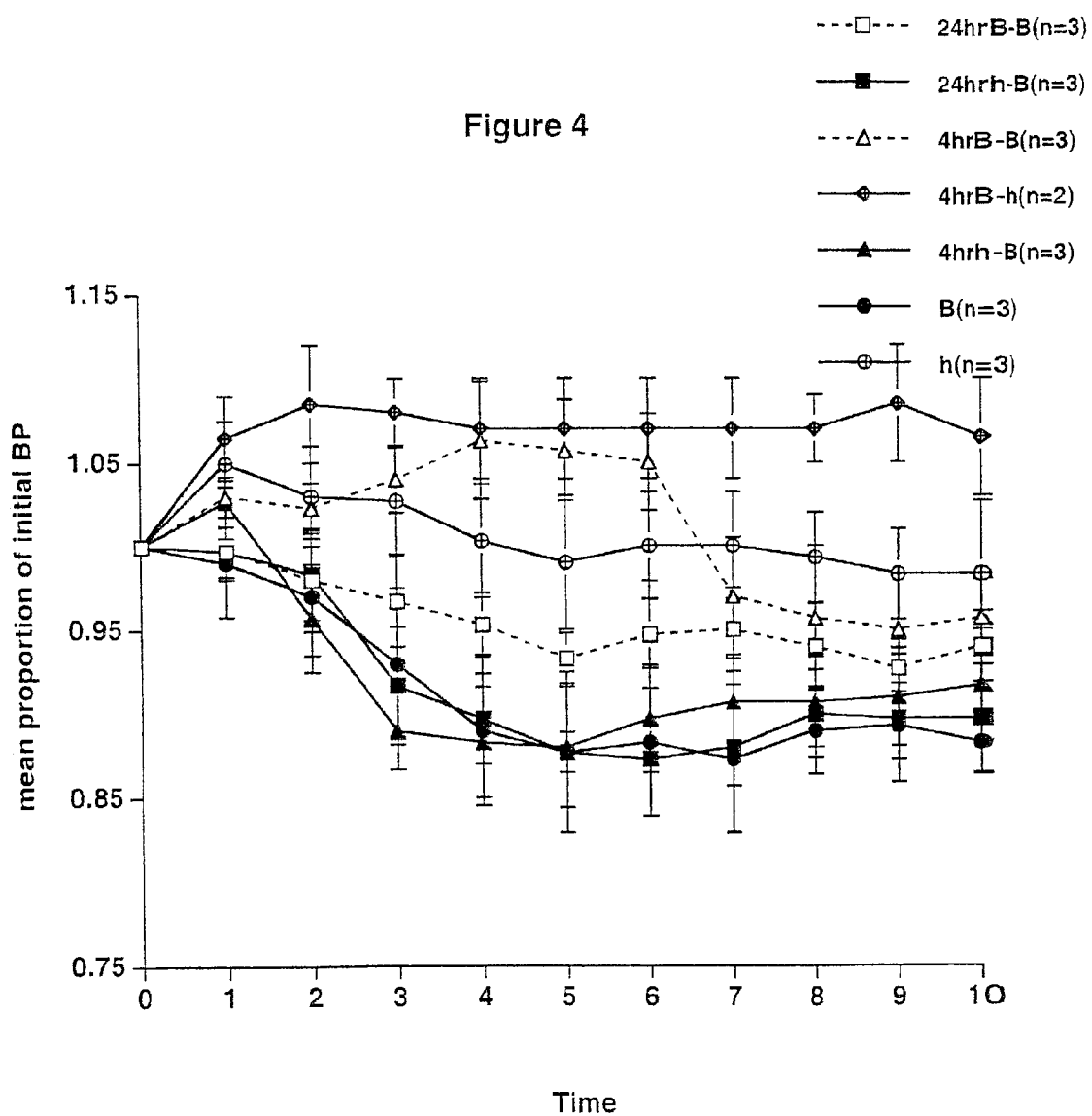
FIG. 4. Ang1-FD-Fc-FD-induced hypotension can be greatly reduced (4 hrB-B group, B=Ang1-FD-Fc-FD ) by pre-treatment with Ang1-FD-Fc-FD 4 hours earlier and slightly reduced (24 hrB-B group) by pre-treatment with Ang1-FD-Fc-FD 24 hours earlier.
Figure 5:
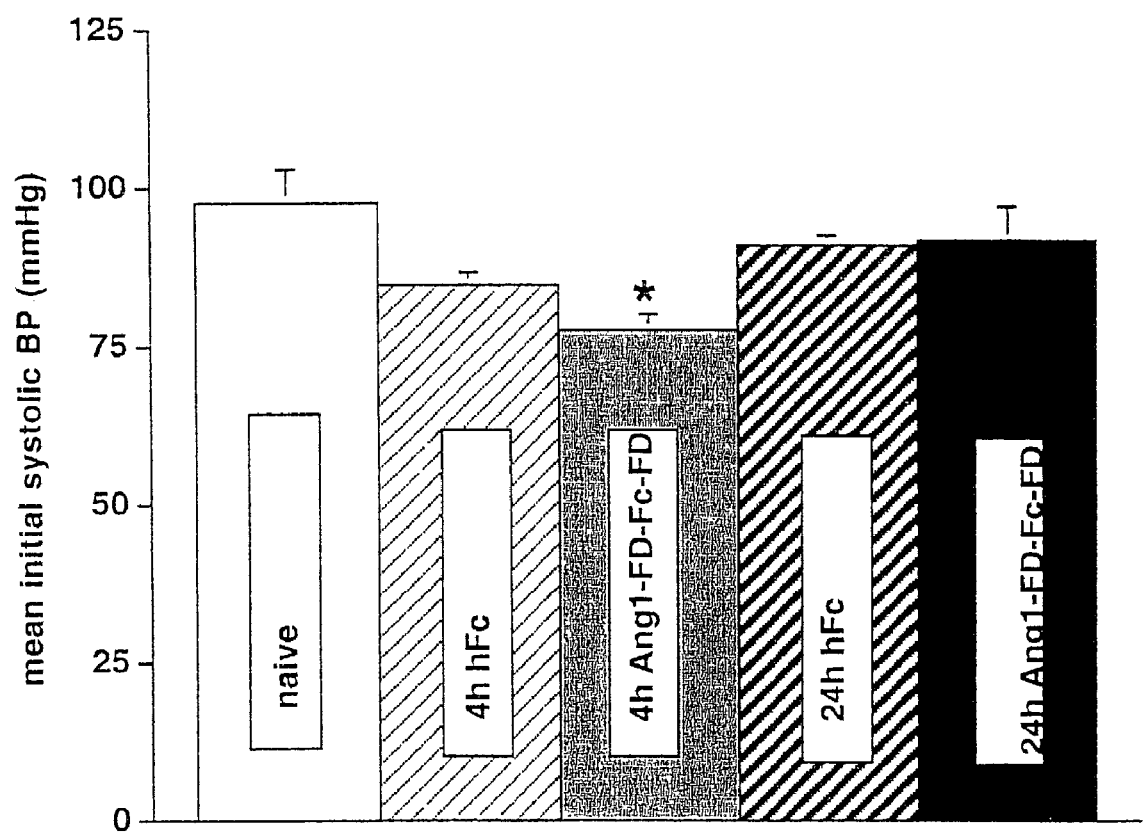
FIG. 5. An i.v. bolus of Ang1-FD-Fc-FD causes a significant decrease in systolic blood pressure that persists after 4 hours, but not after 24 hours.

Ang1-FD-Fc-FD pre-treatment interferes with Ang1-FD-Fc-FD-induced hypotension: To confirm that Ang1-FD-Fc-FD could induce a hypotension refractory state as VEGF can, Applicants administered Ang1-FD-Fc-FD i.v. 4 hours and 24 hours before inducing hypotension with Ang1-FD-Fc-FD. Ang1-FD-Fc-FD administered 4 hours after an initial injection of Ang1-FD-Fc-FD resulted in markedly decreased or no hypotension. 24 hours after Ang1-FD-Fc-FD, Ang1-FD-Fc-FD reliably induced hypotension, but the magnitude of the hypotension still tended to be reduced. The refractory state induced by Ang1-FD-Fc-FD was statistically significant ($F(6,13)=5.985$, $p<0.004$, FIG. 4). Interestingly, Ang1-FD-Fc-FD resulted in significantly decreased initial systolic blood pressure 4 hours after injection, but not 24 hours after injection when it still reduced induced hypotension (FIG. 5). Therefore, Ang1-FD-Fc-FD does induce a refractive state that reduced the magnitude of future inductions that occur within about a day of the initial hypotensive event.

Figure 6:
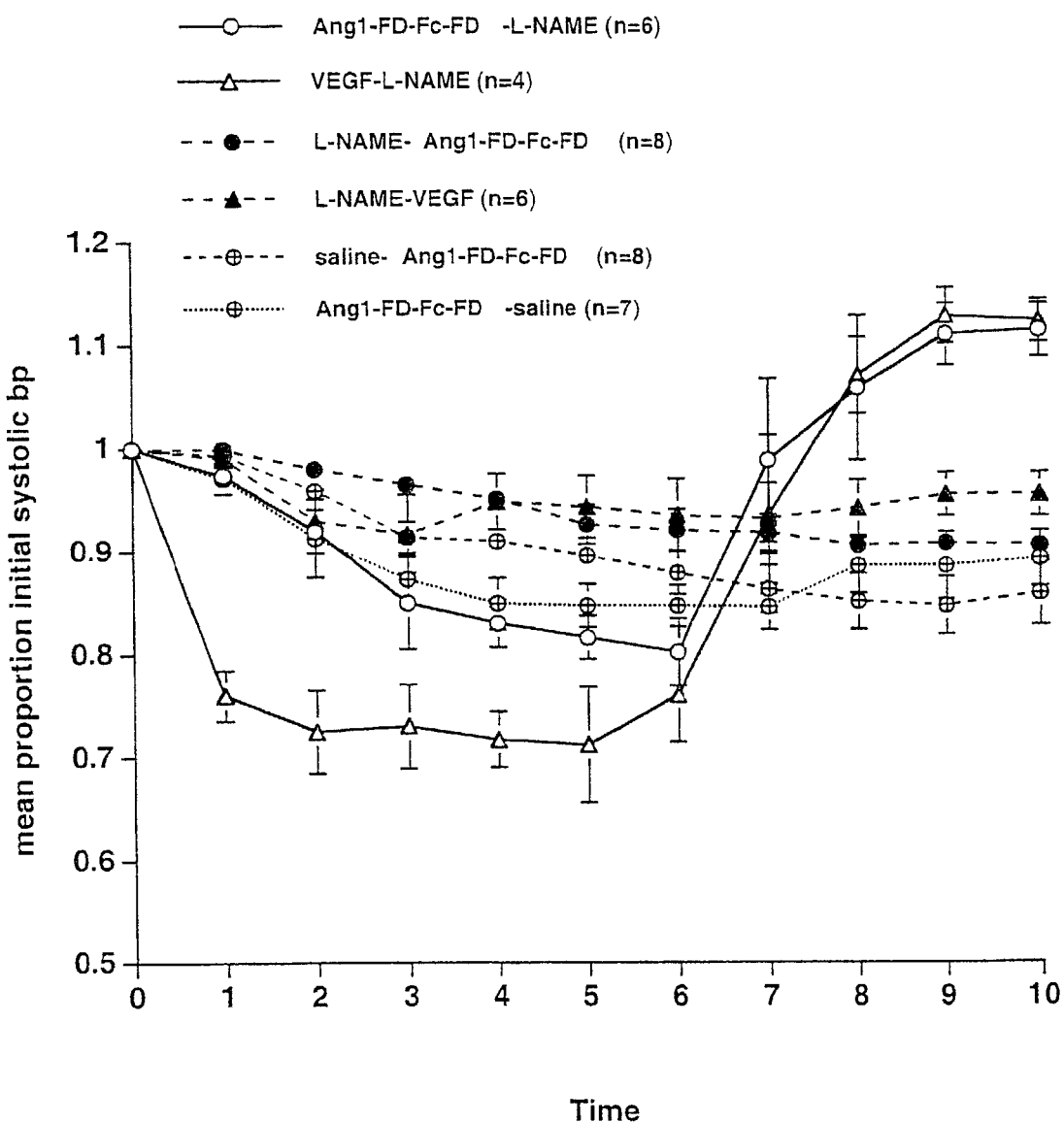
FIG. 6. Ang1-FD-Fc-FD-induced hypotension is dramatically reversed, as is VEGF-induced hypotension, by an i.v. bolus of the nitric oxide inhibitor L-NAME. In addition, Ang1-FD-Fc-FD-induced hypotension is attenuated by pre-treatment with 5 mg L-NAME. The first substance in the legend for each group was administered 6 minutes before the second substance. Time 0 represents the time when either VEGF or Ang1-FD-Fc-FD were injected.
Figure 7:
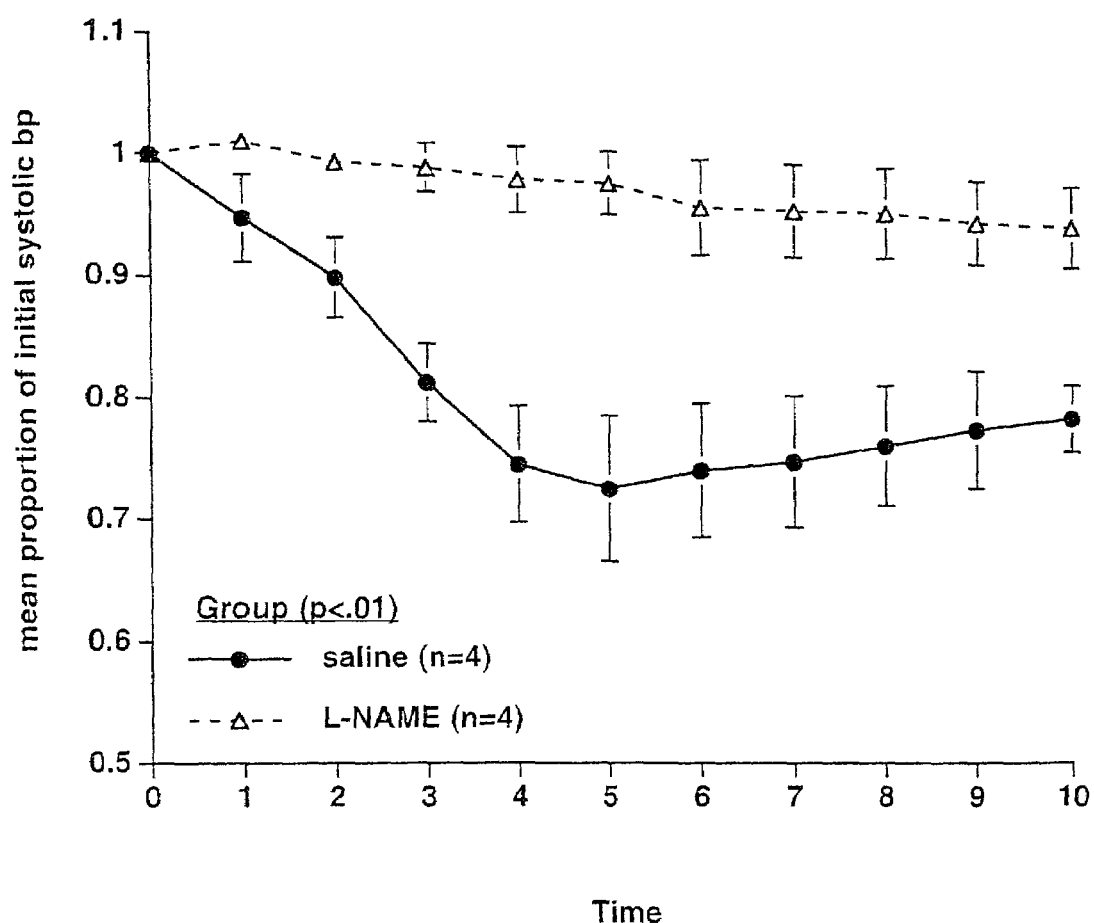
FIG. 7. Ang1-FD-Fc-FD-induced hypotension is almost completely prevented by pre-treatment with the nitric oxide inhibitor L-NAME given 6 minutes prior to Ang1-FD-Fc-FD.

Ang1-FD-Fc-FD-induced hypotension is nitric oxide-dependent: Both VEGF and FGF have been shown to mediate hypotension via nitric oxide-mediated mechanisms. Nitric oxide has been shown to be a potent vasodilatory stimulus, and hence, at least a portion of the reason for decreased blood pressure is probably increased vascular volume. Because Ang1-FD-Fc-FD shows similar hypotension, and has been shown to be involved in at least chronic vascular enlargement, we decided to investigate the possibility that Ang1-FD-Fc-FD acts via nitric oxide-mediated mechanisms. Some animals were pre-treated i.v. with 5 mg of the nitric oxide inhibitor L-NAME 6 minutes before i.v. injection of Ang1-FD-Fc-FD to determine if L-NAME could prevent Ang1-FD-Fc-FD-induced hypotension. Other animals were pre-treated i.v. with 5 mg of L-NAME 6 minutes after i.v. injection of Ang1-FD-Fc-FD to determine if nitric oxide inhibition could reverse Ang1-FD-Fc-FD-induced hypotension. Both pre- and post-treatment with L-NAME significantly interfered with Ang1-FD-Fc-FD-induced hypotension ($F(5,31)=3.542$, $p<0.02$, FIG. 6 and FIG. 7), suggesting that Ang1-FD-Fc-FD causes its hypotensive effect via a nitric oxide-mediated mechanism.

Example 2

Amelioration of Hypertension by Ang1-FD-Fc-Fd

Materials and Methods

Subjects—Male Wistar-Kyoto control rats and male spontaneously hypertensive rats (SHR), 250–350 g, were double-housed in a temperature and humidity-controlled animal housing room. Animals were maintained on a 12:12 light:dark cycle (lights on 06:00). Food and water were available ad libitum.

Systemic injections—Animals that received Ang1-FD-Fc-FD systemically before acute blood pressure measurements were injected with either 25 mg/kg Ang1-FD-Fc-FD or hFc sub-cutaneously 24 hours prior to acute intra-venous injection of VEGF or Ang1-FD-Fc-FD. Animals that received Ang1-FD-Fc-FD systemically during continuous blood pressure monitoring received a single sub-cutaneous injection of Ang1-FD-Fc-FD at 5 mg/kg.

Acute Blood Pressure Measurement—Anesthesia was induced with 2.5% isoflurane in oxygen. Animals were then transferred to a nose cone delivering 1.5–2% isoflurane. Fur was shaved from the left inner thigh and from the right clavicular region. An incision was made in the inner aspect of the thigh, exposing the femoral vein and artery. The femoral artery was isolated and a silicone medical tubing was inserted into the artery. The tubing was filled with heparinized saline and was connected to a blood pressure transducer (IITC). After transduction, the signal was sent to a 4-channel chart recorder (Linseis) for continuous monitoring of pulse and systolic blood pressure. Exact blood pressure values were calculated based on a calibrated standard determined in advance of the surgery using a sphygmomanometer.

After blood pressure stabilized (same value for 1–2 minutes), animals were injected intravenously via the right jugular vein with either 10 μg vascular endothelial growth factor (VEGF) or 40 μg Ang1-FD-Fc-FD. Studies were conducted as follow:

1) 15 μg (equimolar hFc to Ang1-FD-Fc-FD) i.v. hFc in Wistar-Kyoto rats
2) 10 μg i.v. VEGF in Wistar-Kyoto rats
3) 40 μg i.v. Ang1-FD-Fc-FD in Wistar-Kyoto rats
4) 15 μg i.v. hFc in SHRs
5) 10 μg i.v. VEGF in SHRs
6) 40 μg i.v. Ang1-FD-Fc-FD in SHRs For each experiment, animals were monitored for 10 minutes after the acute i.v. bolus.

Chronic Blood Pressure Measurements—SHR rats were chronically implanted with telemetry transmitters to send continuous hemodynamic data to a computer using Data Sciences Dataquest Gold Acquisition software. Animals were anesthetized with isoflurane (2.5–3% induction and 1.5–2% maintenance) in 100% oxygen, and the wound site was shaved, cleaned, and treated with povidone iodine. An incision was made along the midline in the animal's abdomen, taking care not to damage any internal organs. The descending aorta was dissected out and a piece of silk suture was placed around the end of the aorta closest to the renal artery. Pressure was applied to the aorta with the silk suture to prevent blood flow temporarily, and a bent bevel-tipped needle was used to introduce the blood pressure catheter portion of the radiotransmitter into the aorta. The catheter was secured to the aorta with veterinary tissue adhesive. The transmitter was secured to the inner wall of the abdomen with silk suture, and the abdomen was closed with wound clips. Animals were allowed to recover from radiotransmitter implants for at least 2 weeks before measurements were taken. Blood pressure recordings were taken for 24 hours prior to injection of Ang1-FD-Fc-FD to establish a baseline. All animals were then injected with 5 mg/kg Ang1-FD-Fc-FD s.c. The 5 mg/kg dose was used in this experiment due to a protein shortage; however, the typical dose of 25 mg/kg would be expected to produce a larger effect. Animals were then monitored for an additional week.

Data Analysis—For the acute study, the systolic blood pressure was determined for the point immediately prior to the first i.v. injection, and for every minute thereafter. Because animals can have varying initial systolic blood pressures, blood pressures were then normalized to the starting initial blood pressure, which was defined as that which occurred just prior to injection of Ang1-FD-Fc-FD, VEGF, or hFc i.v. Normalized blood pressures were analyzed using a Mixed Factorial ANOVA (treatment×time). For the chronic study, real blood pressures were averaged for each 10 minute time point into 3-hour bins. Analysis of the effect of Ang1-FD-Fc-FD was conducted using a Repeated Measures Factorial ANOVA (treatment phase×time). For all analyses, alpha was set at 0.05.

Results

Figure 8:
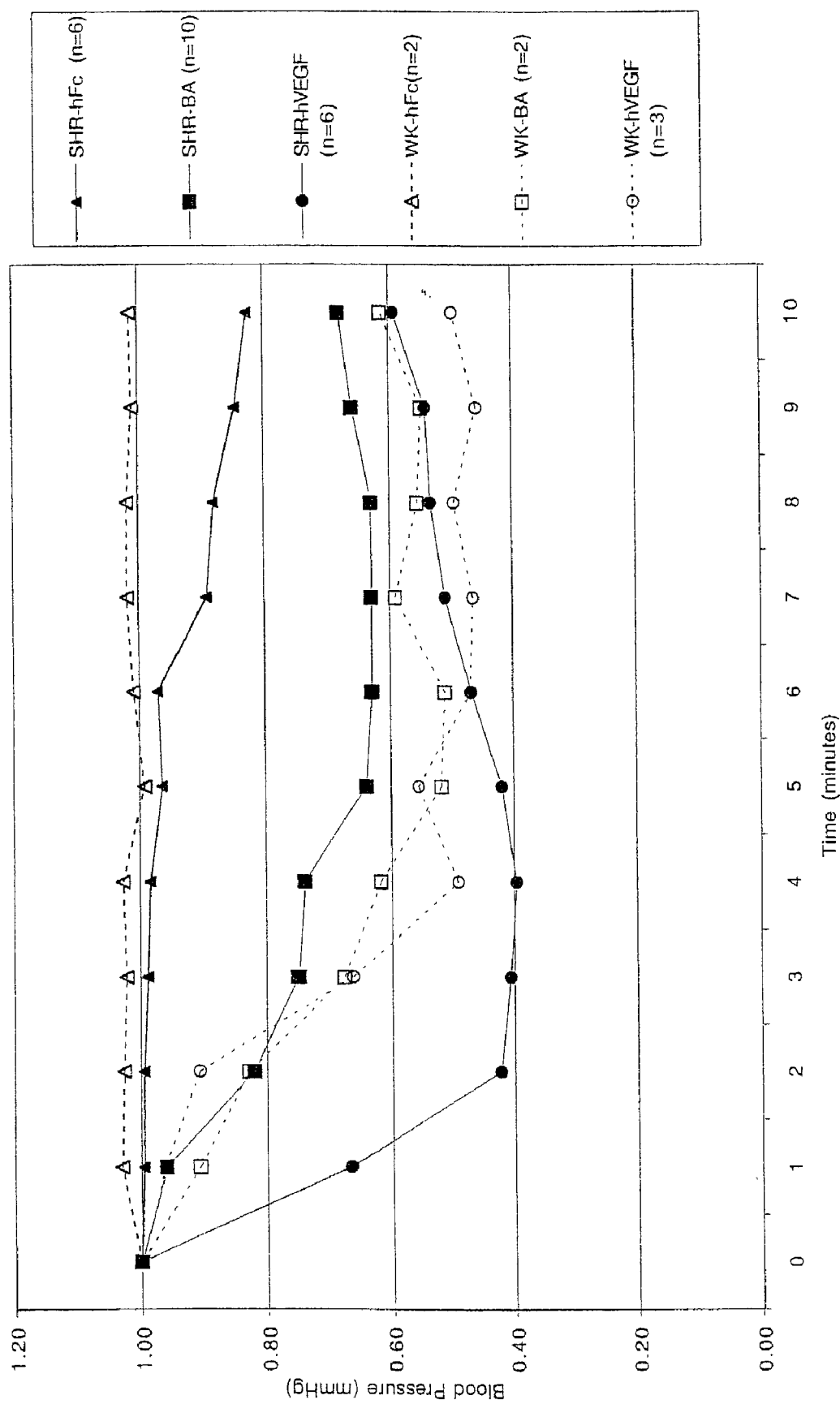
FIG. 8. Both Ang1-FD-Fc-FD and VEGF administered by acute i.v. bolus reverse hypertension in SHR rats and induce hypotension in Wistar control rats. Data are expressed as percentage of mean initial blood pressure. The initial blood pressure in SHR rats averaged about 180 mmHg and the average initial blood pressure in Wistar rats averaged about 90 mmHg. Time 0 represents the time when either Ang1-FD-Fc-FD or VEGF were administered.

Acute Blood Pressure Studies—Both VEGF and Ang1-FD-Fc-FD significantly reduced blood pressure in both Wistar-Kyoto control rats and SHRs. The hFc control protein did not reduce blood pressure in either strain. Ang1-FD-Fc-FD produced a significant 40% decrease in blood pressure in SHRs, bringing their systolic blood pressure from a mean of 186.7 mmHg to 127.5 mmHg within 10 minutes of acute i.v. bolus (the mean normal blood pressure of Wistar-Kyoto control rats was 101.2 mmHg; effect of treatment $F(2,15)=6.033$, $p<0.01$)). The decrease in blood pressure obtained with Ang1-FD-Fc-FD was maintained throughout the measurements (FIG. 8).

Figure 9:
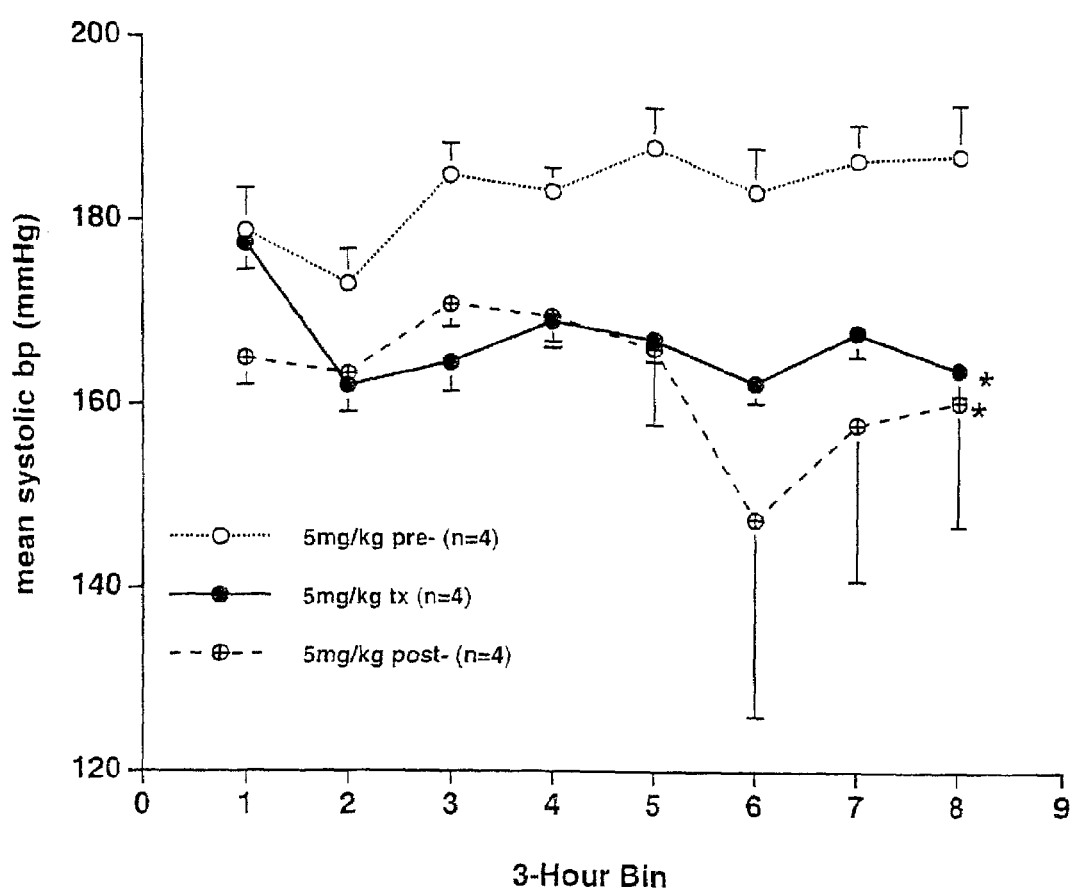
FIG. 9. Ang1-FD-Fc-FD administered s.c. at 5 mg/kg at. The "pre-" line represents systolic blood pressure data obtained by telemetry for the 24 hours preceding the injections of Ang1-FD-Fc-FD. The "tx" line indicates the systolic blood pressure measured during the 24 hours immediately following a single injection of Ang1-FD-Fc-Fd, and the "post-" line represents systolic blood pressure measured in the second day after injections. Although a low dose of Ang1-FD-Fc-FD was used, a significant decrease in blood pressure was observed for 3 days after a single injection.

Chronic Blood Pressure Studies—FIG. 9 illustrates systolic blood pressures in telemetered SHRs for the 24 hours prior to injection with Ang1-FD-Fc-FD (pre), the 24 hours immediately after injection with Ang1-FD-Fc-FD (tx), and the following day (24–48 hours after injection, post). Despite the low dose used (5 mg/kg), Ang1-FD-Fc-FD significantly ameliorated the hypertension in the SHRs within the first 3 hours after s.c. injection ($F(2,9)=4.387$, $p<0.05$). This decrease in blood pressure was maintained for 3 days after injection (first 2 shown on graph). Hence, systemic injection of Ang1-FD-Fc-FD resulted in prolonged and significant decreases in blood pressure in hypertensive rats, even at a low dose.

The following is a summary of the novel findings of the subject invention:

1) TIE-2 activators, for example Ang1-FD-Fc-FD, induce drops in blood pressure in normal and hypertensive animals
2) TIE-2 activator-induced hypotension is long-lasting and mild to moderate
3) TIE-2 activator-induced hypotension is nitric oxide-mediated Thus, based on these novel findings, TIE2 activators, for example Ang1-FD-Fc-FD, may be useful in treating diseases of the vascular system including, but not limited to, hypertension, ischemia, and vascular insufficiencies such as penile erectile dysfunction.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

We claim:

1. A method of attenuating nitric oxide-mediated acute hypertension in a mammal comprising administering to the mammal an effective amount of a TIE2 receptor activator capable of attenuating acute hypertension, wherein the TIE2 receptor activator is Ang1-FD-Fc-FD.

2. A method of attenuating nitric oxide-mediated chronic hypertension in a mammal comprising administering to the mammal an effective amount of a TIE2 receptor activator capable of attenuating acute hypertension, wherein the TIE2 receptor activator is Ang1-FD-Fc-FD.

3. The method of claim 2 wherein the chronic hypertension is pulmonary hypertension.

4. The method of claim 3 wherein the pulmonary hypertension is primary or secondary pulmonary hypertension.

5. The method of claim 2 wherein the mammal is a human.

* * * * *